United States Patent
Maschke

(10) Patent No.: US 8,447,078 B2
(45) Date of Patent: May 21, 2013

(54) X-RAY DIAGNOSTIC DEVICE

(75) Inventor: Michael Maschke, Lonnerstadt (DE)

(73) Assignee: Siemens Aktiengesellschaft, München (DE)

( * ) Notice: Subject to any disclaimer, the term of this patent is extended or adjusted under 35 U.S.C. 154(b) by 1289 days.

(21) Appl. No.: 11/800,027

(22) Filed: May 3, 2007

(65) Prior Publication Data

US 2007/0269001 A1 Nov. 22, 2007

(51) Int. Cl.
*G06K 9/00* (2006.01)

(52) U.S. Cl.
USPC ............... 382/128; 382/129; 378/38; 378/39

(58) Field of Classification Search
USPC .................... 382/128, 129; 378/38, 39
See application file for complete search history.

(56) References Cited

U.S. PATENT DOCUMENTS

| | | | |
|---|---|---|---|
| 5,646,525 A | 7/1997 | Gilboa | |
| 5,666,391 A | 9/1997 | Ohnesorge et al. | |
| 5,745,542 A * | 4/1998 | Gordon et al. | 378/4 |
| 6,125,193 A * | 9/2000 | Han | 382/131 |
| 6,233,476 B1 | 5/2001 | Strommer et al. | |
| 6,246,742 B1 * | 6/2001 | Besson et al. | 378/8 |
| 6,496,558 B2 | 12/2002 | Graumann | |
| 6,600,801 B2 | 7/2003 | Raupach | |
| 6,623,161 B2 * | 9/2003 | Aufrichtig et al. | 378/207 |
| 6,674,835 B2 * | 1/2004 | Kaufhold et al. | 378/53 |
| 7,295,691 B2 * | 11/2007 | Uppaluri et al. | 382/130 |
| 2001/0031919 A1 | 10/2001 | Strommer et al. | |
| 2005/0226375 A1 * | 10/2005 | Eberhard et al. | 378/62 |
| 2006/0050845 A1 * | 3/2006 | Juni | 378/51 |
| 2006/0120507 A1 | 6/2006 | Brunner et al. | |
| 2008/0044076 A1 * | 2/2008 | Spies | 382/132 |

FOREIGN PATENT DOCUMENTS

| | | |
|---|---|---|
| DE | 100 08 053 A1 | 9/2001 |
| DE | 100 51 462 A1 | 4/2002 |
| DE | 100 36 143 C2 | 12/2003 |
| DE | 102 24 011 A1 | 12/2003 |
| DE | 10 2004 029 009 A1 | 1/2006 |
| DE | 10 2004 057 308 A1 | 7/2006 |
| EP | 1 259 162 B1 | 11/2002 |
| EP | 1 443 858 B1 | 8/2004 |
| EP | 1 452 137 B1 | 9/2004 |

OTHER PUBLICATIONS

L.A. Feldkamp, L.C. Davis and J.W. Kress; "Practical cone-beam algorithm"; Optical Society of America; Jun. 1984; pp. 612-619; vol. 1, No. 6.

(Continued)

*Primary Examiner* — Kimyen Vu
*Assistant Examiner* — Ruiping Li

(57) ABSTRACT

There is described an X-ray diagnostic device for performing cephalometric, dental or orthopedic examinations on a patient who is seated or standing. The X-ray diagnostic device comprises an X-ray emitter and an image detector embodied as a flat-panel detector that are arranged situated opposite each other on an orbitally moveable mount. The X-ray diagnostic device further comprises means for adjusting the height of the X-ray emitter and the image detector, a digital image system for recording a projection image using rotation angiography, a device for image processing for reconstructing the projection image into a 3D volume image; and a device for correcting physical effects or artifacts for representing soft tissue in the projection image and in the 3D volume image reconstructed therefrom.

16 Claims, 2 Drawing Sheets

OTHER PUBLICATIONS

Alexander Katsevich; "A General Scheme for Constructing Inversion Algorithms for Cone Beam CT"; IJMMS; 2003; pp. 1305-1321.

Frank Natterer, Frank Wübbeling; "Mathematical Methods in Image Reconstruction"; Society for Industrial and Applied Mathematics; 2001; pp. 1-137; Philadelphia, Pennsylvania.

Karl Wiesent, K. Barth N. Navab, P. Durlak, T. Brunnner, O. Schuetz, and W. Seissler; "Enhanced 3-D-Reconstruction Algorithm for C-Arm Systems Suitable for Interventional Procedures"; May 2000; pp. 391-403; vol. 19, No. 5.

B. Ohnesorge, T. Flohr, K. Schwarz, J.P. Heiken K.T. Bae; "Efficient correction for CT image artifacts caused by objects extending outside the scan field of view"; Medical Physics; Jan. 2000; pp. 39-46; vol. 27, No. 7.

Krishnakumar Ramamurthi and Jerry Prince; "Tomographic Reconstruction for Truncated Cone Beam Data Using Prior CT Information"; MICCAI; 2003; pp. 134-141.

Ruola Ning, Xiangyang Tang and D.L. Conover; "X-Ray Scatter Suppression Algorithm for Cone Beam Volume CT"; Medical Imaging 2002; Proceedings of SPIE vol. 4682; 2002; pp. 774-781.

Harrison H. Barrett, William Swindell; "Radiological Imaging—The Theory of Image Formation, Detection, and Processing"; 1981; pp. 375-464; vol. 2; Chapter 7; Academic Press.

\* cited by examiner

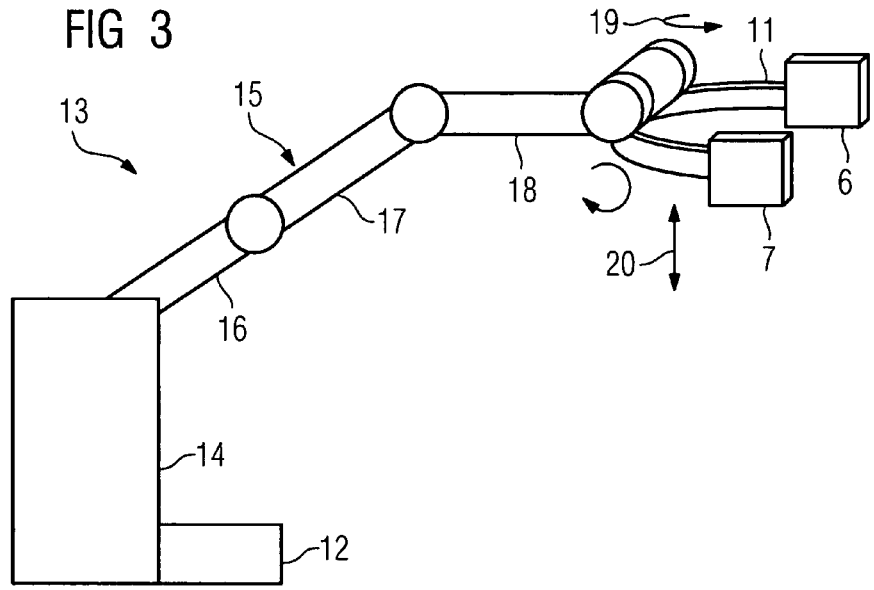
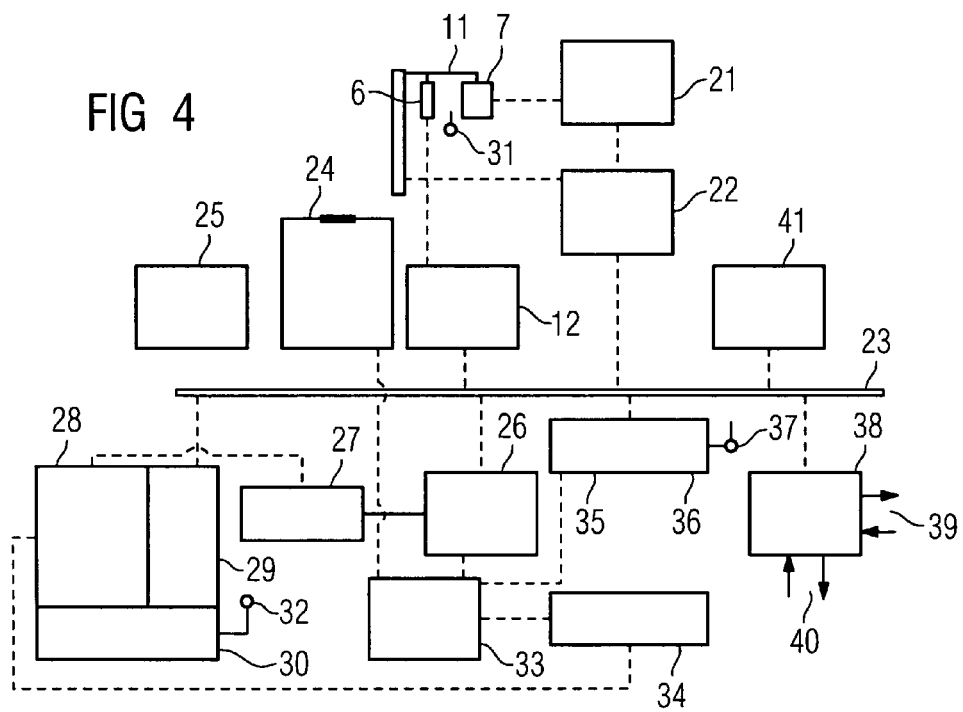

X-RAY DIAGNOSTIC DEVICE

CROSS REFERENCE TO RELATED APPLICATIONS

This application claims priority of German application No. 10 2006 021 373.4 DE filed May 8, 2006, which is incorporated by reference herein in its entirety.

FIELD OF INVENTION

The invention relates to an X-ray diagnostic device for performing cephalometric, dental or orthopedic examinations on a patient who is seated or standing.

BACKGROUND OF INVENTION

Dental and orthopedic disorders occur very frequently, so in the event of said disorders fast and reliable diagnosis and directly initiated therapy are of particular importance for the healing process.

The diagnosing of disorders of said type is supported by imaging methods, with an X-ray or CT examination frequently being performed for the relevant purpose. What, though, is disadvantageous is that CT examinations can be carried out only on a patient who is in a lying position; moreover, a CT device is a relatively expensive examination modality requiring a large amount of space.

For examinations of the cranium or teeth and for orthopedic examinations there are already X-ray devices that enable an examination to be performed on a patient who is seated or standing. Said devices allow a plurality of projections to be recorded in a rotational plane and join the recorded images into a panoramic display. In other embodiments, what is termed layer recording is performed by means of said devices by producing a cumulative image of the object being examined through a rotational movement of an emitter and an X-ray detector. Instances of known systems can be found in EP 1 443 858 B1, EP 1 259 162 B1, and EP 1 452 137 B1.

It is also known how to record 3D angiographic images with the aid of an X-ray device having a C-arm. It is, though, then always necessary to inject a contrast medium into the vessel being examined. All known solutions suffer from not being able to provide a good display of soft tissue.

SUMMARY OF INVENTION

An object of the invention is thus to disclose an X-ray diagnostic device enabling an improved representation of soft tissue.

Provided for achieving said object is an X-ray diagnostic device of the type cited in the introduction that has the following features:
- an X-ray emitter and an image detector embodied as a flat-panel detector that are arranged situated opposite each other on an orbitally moveable mount;
- a means for adjusting the height of the X-ray emitter and the image detector;
- a digital image system for recording a projection image using rotation angiography;
- a device for image processing for reconstructing the projection image into a 3D volume image; and
- a device for correcting physical effects or artifacts for representing soft tissue in the projection image and in the 3D volume image reconstructed therefrom.

The inventive device makes cephalometric, dental, and orthopedic examinations possible on a patient who is seated or standing and achieves a particularly good representation of soft tissue without the need for a contrast medium.

The method performed by the inventive X-ray diagnostic device is similar to the methods known for CT systems, although in CT systems the X-ray emitter and X-ray detector rotate within a closed circular gantry. The use of the inventively provided mount to which the X-ray emitter and flat-panel detector are attached requires additional image processors and special adaptations and expansions of the known image processors.

A means that can include a vertically moveable support arm attached to a stand is provided on the inventive X-ray diagnostic device for adjusting the height of the X-ray emitter and the image detector. The stand can be embodied as a floor stand or ceiling mount.

It can alternatively or additionally be provided on the inventive X-ray diagnostic device for the height-adjusting means to include a robot arm having at least one articulated joint, preferably a plurality thereof.

The device for correcting physical effects or artifacts can be embodied in such a way as to perform at least one correction from the group comprising truncation correction, scatter correction, blooming correction, ring artifact correction, and correcting beam hardening and low-frequency drop.

According to the invention, the device for correcting can have a separate correction processor.

The device for correcting can advantageously be embodied in such a way as to effect calibration of the image recording system, for example geometry, distortion correction, intensity and/or gain calibration.

It has proved advantageous for the device for correcting to be embodied in such a way as to effect a correction of movements performed by the patient and/or his/her organs.

In the inventive X-ray diagnostic device the mount can include a C-arm, with the X-ray emitter and image detector being positioned on the ends of the C-arm.

The flat-panel detector can be produced based on amorphous silicon or on selenium or made from organic photodiodes or phototransistors. According to an advantageous development of the invention, the X-ray diagnostic device can include an ergometer, in particular a bicycle ergometer, or a traveling belt.

BRIEF DESCRIPTION OF THE DRAWINGS

Further advantages and specifics of the invention will be explained with the aid of exemplary embodiments with reference to the figures, all of which are schematics.

FIG. 3 shows a third exemplary embodiment of an inventive X-ray diagnostic device; and FIG. 4 shows the principal constituents of the inventive X-ray diagnostic device.

DETAILED DESCRIPTION OF INVENTION

Figure 1:
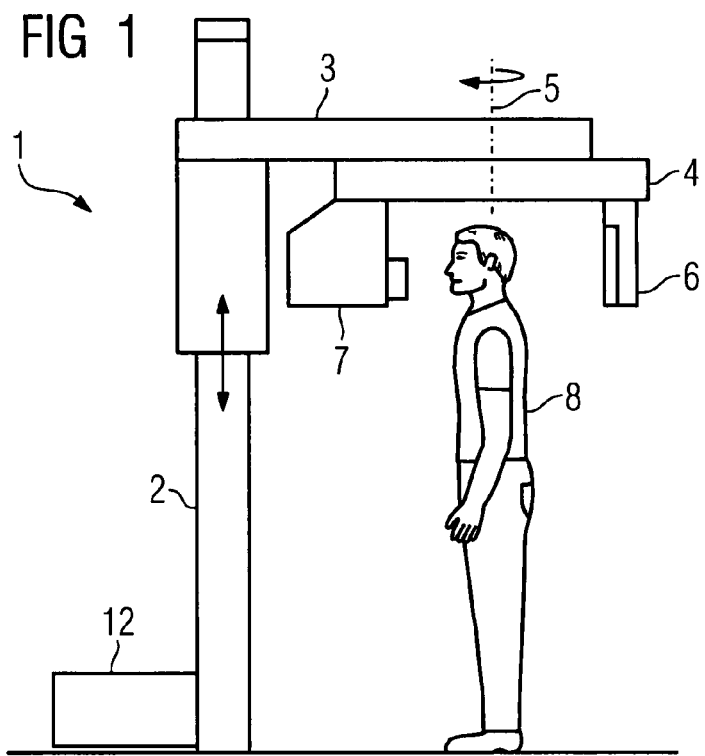
FIG. 1 shows a first exemplary embodiment of an inventive X-ray diagnostic device.

The X-ray diagnostic device 1 shown in FIG. 1 includes a stand 2 that is embodied as a floor stand and to which is attached a height-adjustable support arm 3. The support arm 3 is embodied as a boom; a second support arm 4 is attached thereto. The second support arm 4 is rotatable around a vertical axis 5. Attached to one end of the support arm 4 is an image detector embodied as a flat-panel detector 6. Attached to the other end of the support arm 4 is an X-ray emitter 7. The X-ray emitter 7 or, as the case may be, emitter unit includes an X-ray tube, a diaphragm, and a filter. As is shown in FIG. 1, the cranium of a patient 8 can be examined by means of the X-ray diagnostic device 1; dental or orthopedic examinations can also be performed on a patient who is in a seated or lying position. The support arm 4 and hence the flat-panel detector 6 and X-ray emitter 7 rotate during the examination so that projection images are recorded in rapid succession from different projections.

Figure 2:
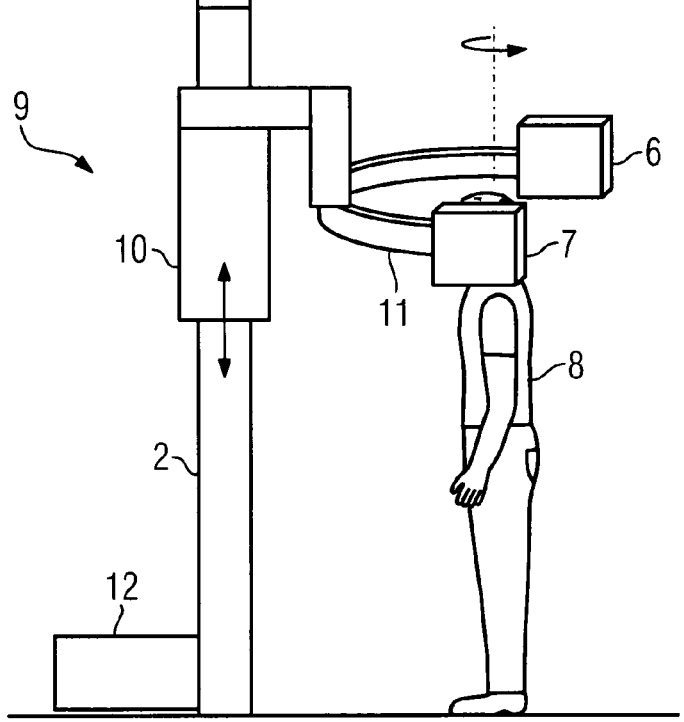
FIG. 2 shows a second exemplary embodiment of an inventive X-ray diagnostic device.

FIG. 2 shows a second exemplary embodiment of an X-ray diagnostic device, with corresponding components being identified by means of the same reference numerals as in FIG. 1. The X-ray diagnostic device 9 shown in FIG. 2 includes a stand 2 on which is located a height-adjustable support arm 10. The flat-panel detector 6 and X-ray emitter 7 are attached to a mount embodied as a C-arm 11. During the examination the C-arm 11 performs a rotational movement around the head of the patient 8 or around another part of the body requiring to be examined. Also forming a constituent of the X-ray diagnostic device 9 is a schematically shown, optional preprocessing and interface unit 12 via which the recorded measurement data is forwarded.

FIG. 3 shows a third exemplary embodiment of the invention.

The X-ray diagnostic device 13 includes a base body 14 to which is attached a multi-part support arm 15. In the exemplary embodiment shown, the support arm 15 includes three support arm sections 16, 17, 18 which, as in the case of a robot arm, are joined in an articulated manner to each other or, as the case may be, to the base body 14. Located on the end of the outermost support arm section 18 is the C-arm 11 having the flat-panel detector 6 and X-ray emitter 7. The X-ray diagnostic device 13 is, owing to the plurality of articulated joints, particularly flexible and can be precisely adjusted to the area on a patient requiring to be examined. The C-arm's direction of rotation is indicated by the arrow 19 and its height adjustability by the double arrow 20. The articulated joint located between the support arm section 18 and C-arm 11 also allows the C-arm 11 to be tilted and inclined. As with the other exemplary embodiments, a preprocessing unit 12 is provided for exchanging data.

FIG. 4 shows the principal constituents of the X-ray diagnostic device.

The X-ray diagnostic device has a flat-panel detector 6 and an X-ray emitter 7 that are arranged on the C-arm 11 that is shown only schematically in FIG. 4. The flat-panel detector 6 is a flat rectangular or square semiconductor detector made from amorphous silicon (aSi).

A high-voltage generator 21 is connected to a system controller 22 and drives the X-ray emitter 7. The system controller 22 is furthermore linked to the flat-panel detector 6 for synchronously controlling the X-ray emitter 7 when the flat-panel detector 6 is ready to record. The system controller 22 likewise controls motors of the C-arm 11 that are attached to the stand or, as the case may be, support arm and registers the feedback message reporting the position of the C-arm 11.

The image data read out from the flat-panel detector 6 is processed in the preprocessing unit 12 and fed to a data bus 23 for further distribution. The system controller 22 and preprocessing unit 12 can form part of an image system. They can furthermore be implemented as separate hardware or software.

When a patient is positioned in the beam path of the X-ray emitter 7, that will in keeping with the X-ray transparency result in an attenuation of the X-rays registered by the flat-panel detector 6.

Physiological sensors, for example ECG electrodes and/or respiration sensors, can be attached to the patient. Said ECG electrodes are linked to a physiological signal processing means 24. A power supply unit 25 supplies the individual devices with the voltages they require.

The image data of the signals, processed by the preprocessing unit 12, of the flat-panel detector 6 is fed to an image processing unit 26 for X-ray images. Said unit is on the one hand linked via a 2D processing means 27 to a 2D-3D display unit 28. Together with an input unit 29 (user I/O) and a 3D display drive 30, said 2D-3D display unit 28 forms a playback unit.

So that account can be taken of the patient's movements during the examination, a sensor 31 is provided that registers said movements. It is positioned on or near the patient. The sensor 31 interacts with a receiver 32, coupled to the 3D-display drive 30, for the patient's movements.

The image processing unit 26 is furthermore linked to a correction device 33 for image artifacts and images. The output signals of said correction device 33 are fed via a 3D image reconstruction means 34 to the 2D-3D display unit 28 for three-dimensional displaying.

Also connected to the data bus 23 are a calibration unit 35 and a position sensor interface 36 that is linked to a receiver 37 which receives signals of the sensor 31 for the patient's movements. The sensor 31 is able to recognize movements of the patient by means of, for example, ultrasound and forwards these via, for examples radio to the receiver 37.

Connected to the data bus 23 for external communication is a DICOM interface 38 which exchanges patient data with the HIS (Hospital Information System) 39 over data lines and image data over further data lines 40 by means of the hospital's intranet or over the internet. The DICOM interface 38 can have the MPPS (Modality Performed Procedure Step) function.

Further connected to the data bus 23 is an image data memory 41 that buffers the image data supplied by the preprocessing unit 12 so said data can then be accessed by the image processing unit 26 and/or forwarded over the DICOM interface 38.

All the processors can be implemented as separate hardware or software and integrated in the image system.

What is thus provided is an X-ray diagnostic device for performing cephalometric, dental or orthopedic examinations on a patient who is seated or standing that includes an X-ray emitter 7 and an image detector embodied as a flat-panel detector 6, with the X-ray emitter 7 and flat-panel detector 6 being arranged situated opposite each other on an orbitally moveable mount. The mount is embodied preferably as a C-arm 11. The X-ray emitter 7 and flat-panel detector 6 are height-adjustable. A digital image system for recording a projection image using rotation angiography is employed. Also used is an image processing unit 26 for reconstructing the projection image into a 3D volume image. Also provided according to the invention is a correction device 33 for compensating or suppressing physical effects or artifacts for displaying soft tissue in the image and in the reconstructed 3D volume image resulting therefrom, which device is supported by the 2D processing means 27, the 3D image reconstruction means 34, the calibration unit 35, and the position sensor interface 36.

During the examination the C-arm 11 having the flat-panel detector 6 and X-ray emitter 7 is turned preferably at least through an angular range of 180° plus fan angle, with the flat-panel detector 6 recording projection images from different projections in rapid succession. Reconstruction can also take place only from a partial range of said recorded data.

For 3D reconstruction, two-dimensional (2D) cone beam projections of a three-dimensional (3D) object are recorded by means of the C-arm 11 during a partial circling operation. From said set of 2D projections it is possible to calculate or estimate the underlying 3D object function using, for example, the Feldkamp algorithm, which is described in "Practical cone-beam algorithm", by L. A. Feldkamp, L. C. Davis, and J. W. Kress, in J. Opt. Soc. Am. A, Vol. 1, No. 6, pp. 612 to 619, 1984. With this method, which is based on the "filtered back projection" principle, it is, however, only possible to mathematically precisely calculate at most one layer, namely that lying within the orbit of the circling operation: the midplane. Layers lying outside the midplane can be calculated only approximately. That is because not all the data needed for precisely calculating layers lying outside the midplane can be gathered during a circling operation. Notwithstanding this limitation, the Feldkamp algorithm at present offers an attractive compromise between computing overhead and result. Mathematically more accurate results can be achieved using precise 3D-reconstruction methods. Of particular interest therein are efficient, precise 3D-reconstruction methods based likewise on filtered back projection such as are known from, for instance, "A general scheme for constructing inversion algorithms for cone beam CT", by A. Katsevich, from Int. J. Math. Math. Sci. 21, pp. 1305 to 1321, 2003.

The 3D image reconstruction is performed using, for example, the Feldkamp algorithm. It is also possible to use other algorithms for reconstructing, for example 3D Radon Inversion (Grangeat's algorithm), Defrise-Clack Filtered Back Projection, Fourier methods, or iterative methods such as are described in, for example, "Mathematical Methods in Image Reconstruction", by F. Natterer and F. Wübbeling in Society for Industrial and Applied Mathematics, Philadelphia 2001.

It is, though, therein necessary to additionally take account of the non-ideal focus and detector path trajectories. A reconstruction method that encompasses the non-ideal C-arm geometry and the partial circling operation has been described by K. Wiesent et al. in "Enhanced 3-D Reconstruction Algorithm for C-Arm Systems Suitable for Interventional Procedures", IEEE Trans. Med. Imaging, Vol. 19, No. 5, May 2000, pp. 391 to 403. Alternatively, other analytic cone beam methods and algebraic and/or statistical reconstruction methods can be used.

The artifact and correction processors consist of a plurality of partial processors that can consist of hardware, software, or a combination of hardware and software. The respective processors can be deactivated individually. The sequence in which said corrections are carried out is selectable and configurable in terms of its parameters so that a variety of examinations having different parameters can be stored then activated by entering the examination name, and the entire X-ray system, including image processing and image/data distributing, is parameterized and preset via the network.

The following artifact and correction processors are used as the correction device 33 for image artifacts and images:

Processors for Calibrating the Recording System

The calibration of the recording system that is to be performed at the beginning consists of a plurality of parts:
1. Geometry calibration:
    Geometry calibration serves to determine the X-ray optics, which is to say the position of the X-ray focus and the position and orientation of the flat-panel detector 6, for each projection. That is important for obtaining reconstructions that have a high spatial resolution and are free from artifacts because, due to instabilities, a C-arm X-ray system can display deviations from the ideal circular path.
2. Distortion correction for X-ray amplifiers only, not necessary for flat-panel detectors:
    The projection images of the X-ray image amplifier exhibit distortions due in part to the earth's magnetic field and in part to shortcomings in the electron optics. Said distortions are eliminated by means of a correction method.
3. Intensity calibration:
    With intensity calibration, each gray-scale value in the projection image is assigned an intensity I and (when the intensity $I_0$ without the object has been determined) a line integral $p=\ln(I_0/I)$. Said line integrals are the input for the respective reconstruction algorithm.
4. Gain calibration:
    A gain is calibrated for the flat-panel detector 6 with the aid of what is termed a flat field image. Said gain calibration is important for suppressing fixed pattern noise that gives rise to artifacts in the reconstructed image (for example ring artifacts). Each measured projection is for that purpose corrected with the flat field image.

Truncation Correction

Every practical X-ray recording device has an X-ray image detector of finite size. That means that objects whose projection exceeds the dimensions of the X-ray image detector can no longer be registered completely and the result is what are termed truncated projections. It is generally not possible to precisely reconstruct a 3D object function from truncated projections even when the underlying algorithm will in principle allow that for completely recorded projections. Extrapolation methods are known whereby the quality of a reconstructed 3D volume can be improved, as has been described by, for example, B. Ohnesorge, T. Flohr, K. Schwarz, J. P. Heiken, and K. T. Bae in "Efficient correction for CT image artifacts caused by objects extending outside the scan field of view", Med. Phys., Vol. 1, pp. 39 to 46, 2000. Anyone aiming for more accurate solutions will as a rule have to rely on a priori information, for example a CT dataset (see K. Ramamurthi, J. L. Prince, "Tomographic Reconstruction for Truncated Cone Beam Data Using Prior CT Information", MICCAI (2), pp. 134 to 141, 2003).

Scatter Correction

In contrast to radiography, scatter in the case of CT reconstruction results not only in a poorer signal-to-noise ratio but also in object-dependent gray-scale distortions, such as cupping and bar or shadow artifacts, that can seriously affect both the quantitative accuracy and discernability of low-level contrasts.

In the case of conventional CT devices having detector arrays formed from one or more rows, scatter can be reduced by means of slot-shaped collimators to such an extent as to virtually no longer affect the image. In the case of CT having an area detector, however, the entire irradiated body cross-section acts as a scatter source, with the intensity of the scatter reaching the area detector even possibly exceeding that of the non-attenuated primary radiation. Although the use of an anti-scatter grid can selectively reduce the scatter fraction, it will always still affect the image and so is not negligible (scatter fraction approx. 25% for cranial images, to over 50% for images of the thorax, pelvis or abdomen).

Scatter correction methods consist of two components: a method for estimating the scatter distribution in the detector plane, and a correction algorithm. For estimating the scatter a measuring method employing the known beam stop technique has been proposed by, for example, R. Ning, X. Tang, D. L. Conover in "X-ray scatter suppression algorithm for cone beam volume CT", Proc. SPIE, Vol. 4682, 2002, pp. 774 to 781, which, though, for handleability reasons is scarcely to be recommended for application to the clinical workflow. Other methods are based on computational models that can be adapted with sufficient accuracy to measurements and/or Monte Carlo simulation calculations and result in substantial image improvements. There are computational models that operate directly on projection images and are known from, for example, U.S. Pat. No. 5,666,391, or iterative methods that also allow information to be used from the volume reconstruction that are described in DE 10 2004 029 009 A1.

Blooming Correction

The bit depth of the X-ray image detectors used for C-arm systems is at present relatively low compared to modem CT detectors (12 bits for a CCD camera and 14 bits for a flat-panel detector compared to 18 to 20 bits in the case of CT detectors). The projections therefore frequently contain blooming which in turn results in artifacts in the reconstruction. Said blooming artifacts can be reduced by extrapolating the projection values while at the same time avoiding clipping.

Low-Frequency Drop

Scattered light in the X-ray image detector produces a background in the projection images that corresponds mathematically to a convolution having a point spread function. Said background results in artifacts in the reconstructed image (similar to scatter) and can be corrected by correspondingly deconvoluting the projection data.

Ring Artifact Correction

The measurement data of individual detector pixels will contain measuring errors and variations even if the X-ray image detector 4 has been calibrated with care. Said errors result in ring artifacts in the reconstructed images. By using suitable (radially and circularly acting) filters it is possible to separate a ring image from an object image. The ring structure is initially detected preferably through radial median filtering of the original image followed by subtraction. Other radial smoothing filtering techniques can also be used. Smoothing said image in a circular direction will eliminate the noise component contained therein. The ring image thereby obtained is finally subtracted from the original image.

Correcting Beam Hardening

The effect of an X-ray beam's hardening while penetrating an absorbing object according to H. Barrett, W. Swindell in "Radiological Imaging", Vol. 2, Chap. 7, pp. 375 to 464 is that in axial images the image elements will be reconstructed with reducing gray-scale values toward the center of the image. This cupping, as it is termed, prevents an image from making a homogeneous impression. Cupping will be avoided if the projection data is converted into a notional mono-energetic X-ray beam. Said conversion is carried out for soft tissue in a pr-reconstructive step and for denser objects such as, for example, bone and metal in a post-reconstructive step followed by second image reconstruction.

Processor for Correcting a Patient's Movements

This solution can be based on the calculation of the movement from the existing recorded 2D images or the movement can be determined by way of a sensor attached to the patient and used for image correction. Motion detectors for compensating a patient's movements in conjunction with the electromagnetic locating of medical instruments are known from U.S. Pat. No. 6,233,476 and US 2001/0031919. The sensor 31 attached to the patient and serving as a motion detector is implemented preferably without cabling, for example using "Bluetooth".

Correcting Organ Movements Due to the Beating Heart ("ECG Gating")

The patient's ECG is recorded for that purpose and fed to the image system's correcting unit. Motion artifacts can be computed out of the image reconstruction using appropriate correction algorithms.

Processor for Eliminating Motion Artifacts Due to Respiration

To eliminate respiration artifacts it is possible to use a chest band that is connected to the signal processing means 24 and which determines the respiration amplitude and frequency via corresponding sensors and initiates corrective computations in the image processing unit which computes the motion artifacts out of the image information. The amplitude and frequency can alternatively be calculated from the ECG signal's envelope curve and fed to the image processing unit's correction device 33. The motion artifacts can be computed out of the image reconstruction using appropriate calculations.

The examination flow of the X-ray diagnostic device comprises the following steps:
a) Starting:
  Signing on, identifying, and registering the patient, either manually or via a data interface, for example DICOM.
b) Positioning:
  Positioning the patient
c) Recording:
  Recording a rotation angiograph through at least 180° with at least two projection recordings (increasing the number of projections and angle range will improve image quality)
d) Correction:
  Correcting artifacts by means of the correction processors
e) 3D reconstruction:
  Reconstructing the 3D volume image
f) 3D representation:
  Representing the 3D volume image on a display or projection device
g) Treatment:
  Carrying out the therapeutic measure, preferably minimally invasively
h) Treatment successful?:
  Checking the therapeutic measure by repeating steps c) to f)
i) Documentation:
  Documenting the diagnosis and therapy on an integrated computing unit
j) Finishing:
  Discharging the patient, dispatching and archiving the documented diagnostic and therapy data preferably via a medical data network (for example DICOM-MPPS).

As an alternative embodiment for applications that pose fewer demands on the resolution it is proposed producing the X-ray images from a small number of projections using discrete tomography techniques, particularly after a first 3D image dataset having a high resolution has been produced. A discrete tomography method is described in, for example, DE 102 24 011 A1. That has the advantage that the patient and clinical personnel will be exposed to only a low level of radiation.

Said recordings can additionally be supported by introducing a contrast medium. The recordings can be made optionally using the DSA mode or without DSA.

For displaying 3D recordings the image system contains a 3D display, preferably a flat-panel screen. That solution will allow three-dimensional viewing without the use of an aid such as, for example, 3D spectacles.

The viewer can additionally wear a head band or normal spectacles having position sensors so that the viewer's line of vision will be synchronized with the viewing direction of the 3D object via corresponding processors. An instance of determining a viewer's line of vision and of tracking an image object is described in U.S. Pat. No. 5,646,525.

The 2D or, as the case may be, 3D recordings can alternatively or additionally be projected by means of a projection device (beamer) in 2D or 3D form onto a projection surface, for example a wall of the examination room, as is described in DE 100 36 143 C2.

The examination device contains a DICOM interface 38, including MPPS (Modality Performed Procedure Step), which can process all the image information and patient data.

Said device can be used for producing 3D reconstructions as well as for performing standard 2D X-ray examinations.

It is expedient to integrate a contrast medium injector, for example from the companies Medrad and Tyco Healthcare.

It is furthermore possible to integrate a patient monitoring system for monitoring a patient's vital functions. An alarm can be triggered thereby if specific limits for a patient's vital parameters are undershot or exceeded. A subsystem for administering an anesthetic, for example an anesthesia ventilator, can also be included.

The proposed solution has the advantage that the diagnoses and therapies nowadays performed using a plurality of medical devices will be performed far more safely and quickly using a single system. This solution makes it possible to plan, perform and control the treatment using one device.

Instead of a flat-panel detector 6 as the X-ray image detector it is also possible to use, for example, an X-ray image amplifier having a CCD camera coupled to it. It is true that the inventive rotation angiography will be more difficult to perform therewith because in the case of the X-ray image amplifier a circular image additionally exhibiting distortions on the circular image edge due to geometric distortions on the X-ray image amplifier will be produced. That would necessitate adapting the algorithms for image construction and require additional distortion correction.

The inventive device enhances the diagnostic possibilities of an angiographic examination through the use of angiographic computed tomography (ACT) by means of an angiographic X-ray diagnostic device. CT-like images can be produced thereby during an angiographic procedure.

Neurovascular treatments always carry a risk of complications. Localized bleeding due to aneurysmic ruptures can be visualized by the inventive device during angiographic examinations. The ventricular system of the brain can furthermore be displayed as a support in diagnosing pathological processes. It is also made possible to guide and observe placements during drainage procedures.

The inventive device will provide excellent diagnostic support during abdominal procedures and excellent interventional support in the case also of puncturing and drainage operations.

For oncological applications the inventive device will enable tumors to be visualized in any part of the body so that totally novel methods for performing biopsies or treatments on tumors such as, for example, embolizing or ablating, can be realized.

The invention claimed is:

1. An X-ray diagnostic device for an examination on a patient seated or standing, comprising:
   a X-ray emitter arranged on a mounting device moveable on a circular path;
   a flat-panel image detector situated opposite to the X-ray emitter and arranged on the mounting device;
   a adjustment device to adjust the height of the X-ray emitter and of the image detector;
   a digital image system to record a projection image based upon rotation angiography;
   an image processing device to reconstruct the projection image into a 3D volume image; and
   a correction device to correct physical effects or artifacts by performing truncation correction, scatter correction, blooming correction, ring artifact correction, and low-frequency drop, for representing soft tissue in the projection image and the 3D volume image,
   wherein the correction device effects a correction of a movement of the patient, wherein the movement of the patient is registered by a sensor and transmitted wirelessly to a receiver, and
   wherein the correction device effects a calibration of the X-ray diagnostic device comprising:
      a geometry calibration to determine X-ray optics,
      a distortion calibration for an X-ray image amplifier,
      an intensity calibration for each gray scale value in the projection image by assigning an intensity I and a line integral $p=\ln(I/I_0)$, wherein the intensity $I_0$ is an intensity without the patient has been determined, and
      a gain calibration for the flat-panel image detector to suppress a fixed pattern noise in the 3D volume image.

2. The X-ray diagnostic device as claimed in claim 1, wherein the examination is selected out of the group consisting of: a cephalometric examination, a dental examination, and an orthopedic examination.

3. The X-ray diagnostic device as claimed in claim 1, wherein the adjustment device has a vertically moveable support arm attached to a stand, wherein the stand is selected from the group consisting of: a floor stand and a ceiling mount.

4. The X-ray diagnostic device as claimed in claim 1, characterized in that the adjustment device has a robot arm with at least one articulated joint.

5. The X-ray diagnostic device as claimed in claim 1, wherein the correction device has a separate correction processor.

6. The X-ray diagnostic device as claimed in claim 1, wherein the correction device effects a truncation correction.

7. The X-ray diagnostic device as claimed in claim 1, wherein the correction device effects a scatter correction.

8. The X-ray diagnostic device as claimed in claim 1, wherein the correction device effects a blooming correction.

9. The X-ray diagnostic device as claimed in claim 1, wherein the correction device effects a correction of a low-frequency drop.

10. The X-ray diagnostic device as claimed in claim 1, wherein the correction device effects a ring artifact correction.

11. The X-ray diagnostic device as claimed in claim 1, wherein the correction device effects a correction of beam hardening.

12. The X-ray diagnostic device as claimed in claims 1, wherein the mounting device includes has a C-arm, wherein the X-ray emitter and the flat-panel detector are located on ends of the C-arm.

13. The X-ray diagnostic device as claimed in claim 1, wherein the flat-panel detector is made based upon a technique selected from the group consisting of: amorphous silicon technique, selenium technique, organic photodiode technique, and phototransistor technique.

14. The X-ray diagnostic device as claimed in claim 1, further comprises a device for the patient selected from the group consisting of: an ergometer, and a traveling belt.

15. The X-ray diagnostic device as claimed in claim 1, wherein a 3D display displays a 3D volume image.

16. The X-ray diagnostic device as claimed in claim 1, wherein the detector is the X-ray image amplifier.

\* \* \* \* \*